(12) United States Patent
Bhagwan et al.

(10) Patent No.: US 8,832,095 B2
(45) Date of Patent: Sep. 9, 2014

(54) AUTOMATED INFORMATION DISCOVERY AND TRACEABILITY FOR EVIDENCE GENERATION

(75) Inventors: Varun Bhagwan, San Jose, CA (US); Tyrone W. A. Grandison, San Jose, CA (US); Daniel Frederick Gruhl, San Jose, CA (US); Jonathan Rogelio Razo, Mountain, CA (US)

(73) Assignee: International Business Machines Corporation, Armonk, NY (US)

( * ) Notice: Subject to any disclaimer, the term of this patent is extended or adjusted under 35 U.S.C. 154(b) by 172 days.

(21) Appl. No.: 13/216,915

(22) Filed: Aug. 24, 2011

(65) Prior Publication Data

US 2013/0054625 A1  Feb. 28, 2013

(51) Int. Cl.
*G06F 7/00* (2006.01)
*G06F 19/00* (2011.01)

(52) U.S. Cl.
CPC .................................... *G06F 19/324* (2013.01)
USPC ......................................................... 707/726

(58) Field of Classification Search
CPC .. G06F 19/324; G06F 19/322; G06F 19/3487
USPC ........................... 707/763, 756, 726, 999.006
See application file for complete search history.

(56) References Cited

U.S. PATENT DOCUMENTS

| | | | |
|---|---|---|---|
| 7,610,545 B2 | 10/2009 | Wagner et al. | |
| 7,865,583 B2 | 1/2011 | Cohen et al. | |
| 2002/0082480 A1 | 6/2002 | Riff et al. | |
| 2004/0242972 A1* | 12/2004 | Adak et al. | 600/300 |
| 2007/0106751 A1* | 5/2007 | Moore | 709/217 |
| 2007/0106754 A1* | 5/2007 | Moore | 709/217 |
| 2007/0162311 A1* | 7/2007 | Gentles | 705/3 |
| 2007/0266166 A1 | 11/2007 | Cohen et al. | |
| 2008/0065452 A1* | 3/2008 | Naeymi-Rad et al. | 705/8 |
| 2010/0106522 A1* | 4/2010 | Cooper et al. | 705/3 |
| 2010/0241595 A1 | 9/2010 | Felsher | |
| 2010/0268552 A1 | 10/2010 | Schoenberg et al. | |
| 2011/0015947 A1 | 1/2011 | Erry et al. | |
| 2011/0077973 A1* | 3/2011 | Breitenstein et al. | 705/3 |
| 2012/0059668 A1* | 3/2012 | Baldock et al. | 705/3 |
| 2012/0078062 A1* | 3/2012 | Bagchi et al. | 600/300 |
| 2012/0173285 A1* | 7/2012 | Muthukrishnan | 705/3 |

OTHER PUBLICATIONS

Jamie, Syed Imran, et al., "Information Provenance for Open Distributed Collaborative System", Dec. 12-16, 2009, pp. 737-741, 10th Inernational Symposium on Pervasive Systems, Algorithms, and Networks, IEEE, Kaohsing, Taiwan.

(Continued)

*Primary Examiner* — Mohammed R Uddin
(74) *Attorney, Agent, or Firm* — Ference & Associates LLC (57) ABSTRACT

Described herein are methods, systems, apparatuses and products for automated information discovery and traceability for evidence generation. An aspect provides for accessing a mapping of a plurality of connected nodes stored in a memory device, said mapping being discovered via a network scan based on a seed set, said plurality of connected nodes storing a plurality of archived healthcare records; accessing content stored in a memory device and ingested from said plurality of connected nodes; and determining a longitudinal healthcare record from the mapping and the content ingested from said plurality of connected nodes. Other embodiments are disclosed.

16 Claims, 5 Drawing Sheets

(56) References Cited

OTHER PUBLICATIONS

Alvarez, Sergio, et al., "Applying Provenance in Distributed Organ Transplant Management", IPAW 2006, pp. 28-36, L. Moreau and I. Foster (Eds.), Springer-Verlang Berlin Heidelberg 2006.

Kifor, T., et al., "Provenance in Agent-mediated Healthcare Systems", 2006, 17 pages, IEEE Intelligent Systems, ISSN 1541-1672 (In Press).

Bhagwan, Varun, et al., "MONGOOSE: MONitoring Global Online Opinions via Semantic Extraction", Sep. 21-25, 2009, IEEE International Conference on Cloud Computing, pp. 214-220, 2009 IEEE International Conference on Cloud Computing, Bangalore, India.

Alba, Alfredo, et al., "Accessing the Deep Web: When Good Ideas Go Bad", Oct. 19-23, 2008, pp. 815-818, OOPSLA 2008, ACM, Nashville, Tennessee, USA.

* cited by examiner

AUTOMATED INFORMATION DISCOVERY AND TRACEABILITY FOR EVIDENCE GENERATION

FIELD OF THE INVENTION

The subject matter presented herein generally relates to automated information discovery and traceability for evidence generation.

BACKGROUND

Given the rise of privacy regulation and the proliferation of IT assets (fixed, virtual, mobile), challenges arise for organizations in managing sensitive personal information, such as the personal healthcare information (PHI) governed by government regulatory laws (for example, the Health Insurance Portability and Accountability Act (HIPAA)). Furthermore, an organization should be in an audit-ready position to demonstrate compliance to external regulatory and contractual requirements, as well to demonstrate that internal processes are effective in processing and protecting this information. Based on privacy laws, the owner of a PHI data set may require an organization to provide a report or delete whatever information is being processed and stored. Appropriately managing such sensitive personal information thus poses many challenges to organizations responsible for such data.

BRIEF SUMMARY

One aspect provides a computer program product comprising: a computer readable storage medium having computer readable program code embodied therewith, the computer readable program code comprising: computer readable program code configured to access a mapping of a plurality of connected nodes discovered via a network scan based on a seed set, said plurality of connected nodes storing a plurality of archived healthcare records; computer readable program code configured to access content ingested from said plurality of connected nodes; and computer readable program code configured to determine a longitudinal healthcare record from the mapping and the content ingested from said plurality of connected nodes.

Another aspect provides a method comprising: accessing a mapping of a plurality of connected nodes stored in a memory device, said mapping being discovered via a network scan based on a seed set, said plurality of connected nodes storing a plurality of archived healthcare records; accessing content stored in a memory device and ingested from said plurality of connected nodes; and determining a longitudinal healthcare record from the mapping and the content ingested from said plurality of connected nodes.

A further aspect provides a system comprising: at least one processor; and a memory device operatively connected to the at least one processor; wherein, responsive to execution of program instructions accessible to the at least one processor, the at least one processor is configured to: access a mapping of a plurality of connected nodes, said mapping being discovered via a network scan based on a seed set, said plurality of connected nodes storing a plurality of archived healthcare records; access content ingested from said plurality of connected nodes; and determine a longitudinal healthcare record from the mapping and the content ingested from said plurality of connected nodes.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the claims, but is merely representative of those embodiments.

Reference throughout this specification to "embodiment(s)" (or the like) means that a particular feature, structure, or characteristic described in connection with the embodiment is included in at least one embodiment. Thus, appearances of the phrases "according to embodiments" or "an embodiment" (or the like) in various places throughout this specification are not necessarily all referring to the same embodiment.

Furthermore, the described features, structures, or characteristics may be combined in any suitable manner in different embodiments. In the following description, numerous specific details are provided to give a thorough understanding of example embodiments. One skilled in the relevant art will recognize, however, that aspects can be practiced without certain specific details, or with other methods, components, materials, et cetera. In other instances, well-known structures, materials, or operations are not shown or described in detail to avoid obfuscation.

Modern electronic healthcare information systems are often the result of many years (50 or more in some cases) of record keeping and incremental improvements in the management of healthcare information records. It is not surprising then that they can often become a tangled collection of dozens or even hundreds of historical information archives and repositories. As the value of the longitudinal record extending over decades becomes more evident, both for clinical care as well as comparative effectiveness research, many health organizations are moving to centralized Electronic Health Record (EHR) systems that seek to contain a copy of all information about a patient. Unfortunately, gathering and organizing this historical, archived information can be a challenge. Organizing information sources and tracking the provenance of all information in a patient's EHR involves a combination of tools to best develop an information acquisition scheme for centralization.

Thus, organizations that maintain and/or use Electronic Health Records (HER) or personal healthcare information (PHI) data face a set of challenges. One common challenge is being able to identify and compound an asset inventory, which relies mostly on manual discovery processes that in some cases end up producing an incomplete and inaccurate inventory. Another challenge, and in some cases a bit more difficult one to track, is managing PHI datasets as they move (are copied, transferred, or stored) throughout an organization's IT assets. This is otherwise known as provenance.

The research community has investigated provenance; however healthcare-specific issues involved in using provenance data in medicine have been scantly addressed. Prior work has been focused on generic systems, methods and techniques for efficiently acquiring, tracking, storing and sharing provenance data. Domain-specific work in the space has centered on the issues involved in optimizing provenance stores.

Accordingly, an embodiment addresses the specific and real problem of leveraging existing or generated provenance information for identifying historical/archived assets throughout an organization network domain, and detects the multi-paths that data sets may have followed. An embodiment generates evidence in a healthcare system where there is initially sparse information of data origins. An embodiment leverages an initial set of data nodes in a network, scans for other data nodes in the network, preserves the provenance information, notes the mapping evidence, and uses the information to produce an enhanced and improved evidence platform. An embodiment thus may be used in healthcare clients, where the sources for data have been lost (due to personnel missteps, technology evolution/obsolescence, improper documentation, et cetera). There is currently no way to bootstrap a healthcare environment from such a state to one where it can provide evidence and also document the lineage of its data.

An embodiment provides an evidence platform that organizes, for example in a graph, various historical/archived personal healthcare information records as gathered from various client systems, or nodes. For example, nodes of a graph may represent healthcare content management systems of a wide variety of types. Nodes may include a picture archiving and communications system (PACS), an electrocardiogram (EKG) archive, a database, an electronic healthcare system, textual reports, lab results et cetera. Typically these machines contain either an exact copy of an upstream source, a transformed version of that data, or a subset of that data. For example, the first node might be an EKG server that holds the whole EKG for a patient, a second (separate) node may hold the physician dictated EKG report for the patient, where a downstream node might be an EHR system that contains only a few (presumably significant) values from the original report. Each node will typically have hundreds to hundreds-of-thousands of various reports, potentially spanning many different modalities. Each link or edge in the graph represents a flow of information from one node to the next. For example, an edge might be a daily dump of information from an EKG PACS to a central EHR system.

An embodiment provides a means for user(s) to trace various pieces of personal healthcare information by giving it context. For example, by examining when a report is available in a node, an embodiment may identify which node(s) come before (upstream) or after (downstream) each other in the dataflow. Aggregating and solving for all of these traces allows for a best guess derivation of a complete graph. Once the flow has been captured and derived, it is possible to patch together a representation through time of the data available for a patient. This is referred to herein as a longitudinal record. Traceability is achieved once the flow is derived. Thus, it is then possible to probe each node for reports on a patient, and to ascertain that they have, indeed, propagated to the next node in the flow. Errors or inconsistencies in such propagation can be noted and brought to the attention of an administrator. Additionally, any nodes that do not fit into the graph for lack of supporting evidence or data are also brought to the attention of an administrator, who can manually edit the graph or discard irrelevant nodes.

An embodiment provides provenance information for example by mapping each downstream report to the upstream report that supports it. This allows, for example, a physician to look at a questionable summary report of an EKG, obtained from a given downstream node, and work backwards to the original EKG trace, stored in an upstream system, where the physician might, for example, confirm that there was a loose lead and that the downstream EKG summary report containing an odd value should therefore be disregarded. An embodiment may induce the graph by looking at time stamps of entry into the system when available, or by periodic draws, noting the order in which event reports appeared on various systems.

The description now turns to the figures. The illustrated example embodiments will be best understood by reference to the figures. The following description is intended only by way of example and simply illustrates certain example embodiments representative of the invention, as claimed.

Figure 1:
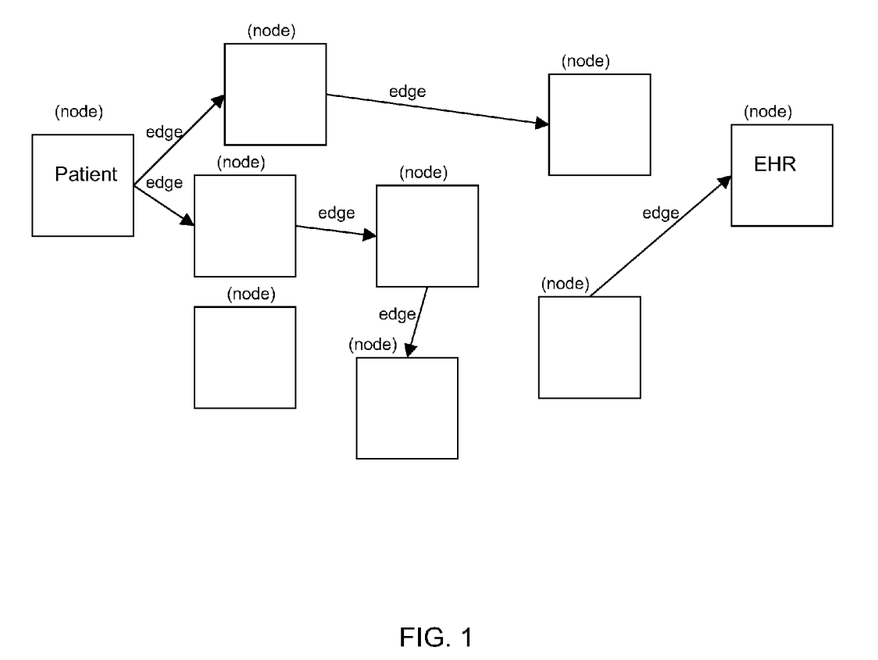
FIG. 1 illustrates an example of sparsely populated healthcare information graph.

Referring to FIG. 1, each archived record (for example, a historical, archived healthcare information record) within a system may be related to other records. However, the relation between the records may not be known. An embodiment seeks to populate the graph with an edge to a source. All sources ultimately terminate, for example at the Patient, but go through a number of steps to get there. Thus, starting with a single node EHR (the root), an embodiment populates it with the modalities and sources known.

An embodiment provides a set of tools that make it possible to fill out such a graph. Without such tooling, the problem may be intractable for human implementation due to no one person knowing where all the information in a clinical environment comes from. Thus, it may be impossible to keep track of all edge cases given the time needed and the regulatory constraints against inspecting vast quantities (potentially in the petabyte range) of private archived patient healthcare records for clues.

Figure 2:
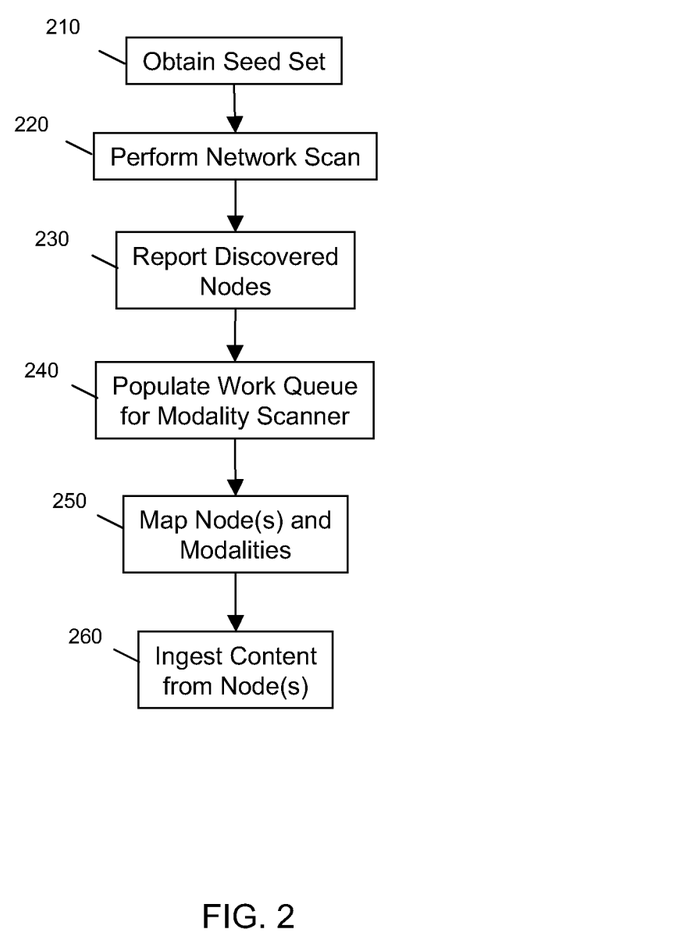
FIG. 2 illustrates an example process for healthcare information system and content discovery.

Referring to FIG. 2, a first step in this process may include an embodiment using the aforementioned known sources as a seed-set 210, and doing a complete network scan 220. The objective is to determine the network-connected nodes within the organization. The set of nodes detected via the node-scan of the network are fed to a central database 230, whose job is to maintain a comprehensive listing of the machines within the organization, the data modality supported by the individual machines, as well as a mapping of any backup/mirror nodes. There are several reasons for keeping tabs on the backups/mirrors within the system. For example, this helps to ensure that the various data ingestors can switch to a backup/mirror if the mainline server is down. Also, this helps to ensure that automated scans of backup nodes do not flag the content as redundant during any resource reduction stages (for example, when servers with unnecessarily duplicated content are to be reclaimed).

The machine database thus generated may be used to populate the work-queue for a modality scanner 240. The modality scanner's job is to probe machines/nodes for the existence of a specific data-type (for instance, in the healthcare-cardiology domain, EKG videos, EKG waveforms, textual reports, structured database content et cetera). It does so by means of applying a set of standard heuristics, such as machine-specific templates for echo videos, histogram checks for image files (EKG), et cetera. The output provides a mapping between a node and zero or more data-modalities supported by the node 250.

Finally, data ingestor(s) are used to fetch content of various modalities from the machines 260. For example, a Mongoose data ingestor suite supports fetching content of various modalities; however, the specific ingestor chosen may be based on the data modality supported by the node from which the data is to be ingested. The Mongoose suite provides various different mechanisms to fetch the data (for example, web-based crawling, RSS-atom feeds, API-based, et cetera). This entire suite of ingestors may be used to fetch any and all possible content from the nodes in the system. It is worth noting that the ingestors certainly do not have to be Mongoose style ingesters. Using Mongoose style ingesters, however, may simplify the process by dealing with intermittently available/functional data sources (nodes).

The data topology also may be captured from a provenance perspective, such that the data flow between the Patient and EHR root is populated. Once the flow has been captured and derived, it is possible to patch together a coherent representation through time of all data available for a patient, that is, to obtain a longitudinal record. Traceability is achieved once the flow is derived. It is then possible to probe each node for reports on a patient, and then to ascertain that they have, indeed, propagated to the next node in the flow. Errors or inconsistencies in such propagation can be noted, and for example, be brought to the attention of an administrator.

Figure 3:
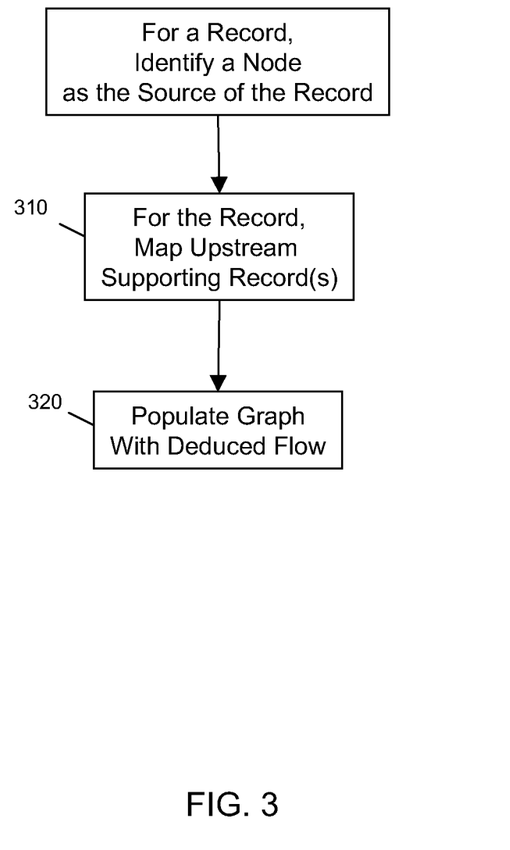
FIG. 3 illustrates an example process for healthcare information graph construction.

For example, referring to FIG. 3, provenance may be obtained by mapping each downstream report (at a particular node) to the upstream report (at an upstream node) that supports it 310. This allows, for example, a physician to look at a questionable report of an EKG, and work backwards to the original EKG trace stored in an upstream system to become familiar with the provenance of the particular summary (or information contained therein). Thus, a graph may be populated 320 with a flow by looking at time stamps of entry into the system when available, and/or by periodic draws, and noting order in which event reports (archived healthcare records) appear on various systems (nodes).

Thus, an embodiment generally provides two phases, an inventory phase (referring to FIG. 2 generally) and a trace phase (referring to FIG. 3 generally). In an inventory phase, all repositories (nodes) are identified and an embodiment gathers a large sample of reports from them. When known, exact edge linkages between nodes may be recorded as well. In a trace phase, an embodiment identifies nodes that contain a patient's record and deduces the data flow by looking at what time the data flowed into a given node.

Figure 4:
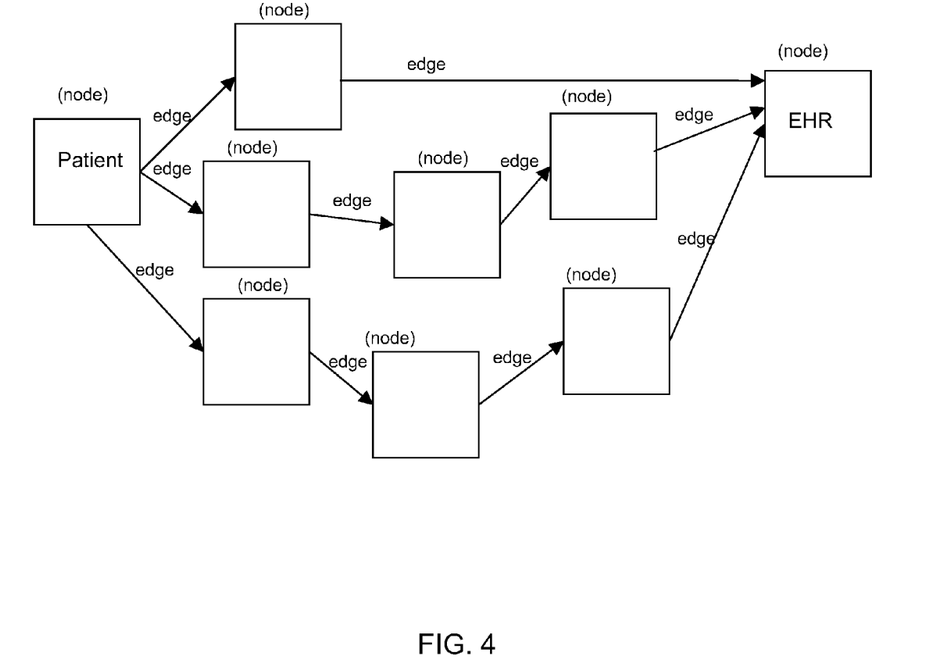
FIG. 4 illustrates an example of a complete healthcare information graph.

Referring to FIG. 4, the various data blocks of the graph may then be filled in and/or corrected (from an initial mapping, referring to FIG. 1 generally) based on the modality of the data found on a given node, as well as the presence of relevant patient identifier(s) in said data. This enables the system to provide access to the longitudinal record of a patient within an organization, as well as support requests for traceability and provenance. Thus, an embodiment may determine when each record entered the system, and what the path that record took through the system, such that it is possible to assemble a time ordered list of data available about a patent (the longitudinal record). An embodiment thus provides the links to the provenance of each record.

Figure 5:
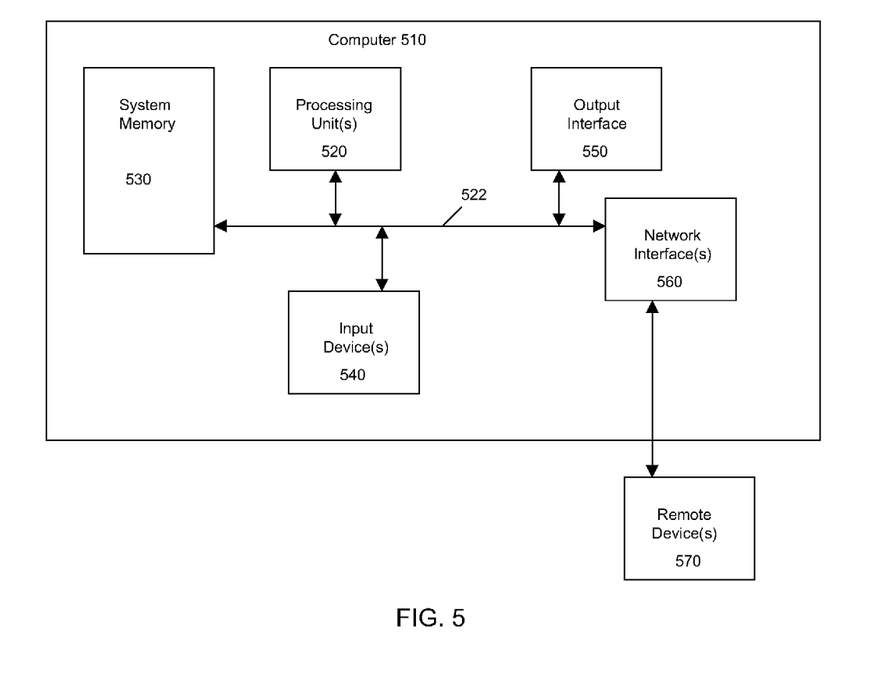
FIG. 5 illustrates an example computing device.

Referring to FIG. 5, it will be readily understood that embodiments may be implemented using any of a wide variety of devices or combinations of devices. An example device that may be used in implementing embodiments includes a computing device in the form of a computer 510. In this regard, the computer 510 may execute program instructions configured to provide automated information discovery and traceability for evidence generation, and perform other functionality of the embodiments, as described herein.

Components of computer 510 may include, but are not limited to, at least one processing unit 520, a system memory 530, and a system bus 522 that couples various system components including the system memory 530 to the processing unit(s) 520. The computer 510 may include or have access to a variety of computer readable media. The system memory 530 may include computer readable storage media in the form of volatile and/or nonvolatile memory such as read only memory (ROM) and/or random access memory (RAM). By way of example, and not limitation, system memory 530 may also include an operating system, application programs, other program modules, and program data.

A user can interface with (for example, enter commands and information) the computer 510 through input devices 540. A monitor or other type of device can also be connected to the system bus 522 via an interface, such as an output interface 550. In addition to a monitor, computers may also include other peripheral output devices. The computer 510 may operate in a networked or distributed environment using logical connections (network interface 560) to other remote computers or databases (remote device(s) 570). The logical connections may include a network, such local area network (LAN) or a wide area network (WAN), but may also include other networks/buses.

As will be appreciated by one skilled in the art, aspects may be embodied as a system, method or computer program product. Accordingly, aspects of the present invention may take the form of an entirely hardware embodiment, an entirely software embodiment (including firmware, resident software, micro-code, et cetera) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for embodiments may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments are described with reference to figures of methods, apparatus (systems) and computer program products according to embodiments. It will be understood that portions of the figures can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Although illustrated example embodiments have been described herein with reference to the accompanying drawings, it is to be understood that embodiments are not limited to those precise example embodiments, and that various other changes and modifications may be affected therein by one skilled in the art without departing from the scope or spirit of the disclosure.

What is claimed is:

1. A computer program product comprising:
 a non-transitory computer readable storage medium having computer readable program code embodied therewith, the computer readable program code comprising:
 computer readable program code configured to access a mapping of a plurality of connected nodes discovered via a network scan based on a seed set, said plurality of connected nodes storing a plurality of archived healthcare records, the seed set comprising an initial mapped set of nodes;
 computer readable program code configured to access content ingested from said plurality of connected nodes; and
 computer readable program code configured to determine a longitudinal healthcare record from the mapping and the content ingested from said plurality of connected nodes;
 wherein to determine a longitudinal healthcare record comprises determining provenance of at least one healthcare record; and
 wherein to determine provenance comprises: probing or scanning nodes in said plurality of connected nodes for at least one archived healthcare record of a patient, determining connectivity of the probed or scanned nodes, and adding to the seed set a mapping of the connectivity of the probed or scanned nodes;
 ascertain if an archived healthcare record for said patient has propagated to a next node in the plurality of connected nodes;
 wherein to determine provenance comprises mapping backup or mirror nodes.

2. The computer program product according to claim 1, wherein said computer readable program code configured to determine a longitudinal healthcare record further comprises:
 computer readable program code configured to identify a source node in said plurality of connected nodes for a particular archived healthcare record.

3. The computer program product according to claim 2, wherein said computer readable program code configured to determine a longitudinal healthcare record further comprises:
 computer readable program code configured to, for said particular archived healthcare record, map at least one upstream record at an upstream node in said plurality of connected nodes supporting said particular archived healthcare record.

4. The computer program product according to claim 3, wherein the particular archived healthcare record comprises one or more of: an exact copy of said upstream healthcare record, a transformed version of the upstream healthcare record, or a subset of data contained in said upstream healthcare record.

5. The computer program product according to claim 3, wherein said computer readable program code configured to determine a longitudinal healthcare record further comprises:
 computer readable program code configured to access a graph comprising data flow connecting a plurality of related, archived healthcare records constructed from said mapping of a plurality of connected nodes.

6. The computer program product according to claim 5, wherein said longitudinal healthcare record comprises a representation through time of data available from said plurality of related, archived healthcare records for a patient.

7. The computer program product according to claim 1, further comprising computer readable program code configured to map at least one modality to at least one of said plurality of connected nodes.

8. The computer program product according to claim 7, further comprising computer readable program code configured to probe at least one node in said plurality of connected nodes for a specific data-type based on at least one modality of said at least one node.

9. A method comprising:
 accessing a mapping of a plurality of connected nodes stored in a memory device,
 said mapping being discovered via a network scan based on a seed set, said plurality of connected nodes storing a plurality of archived healthcare records, the seed set comprising an initial mapped set of nodes;

accessing content stored in a memory device and ingested from said plurality of connected nodes; and determining a longitudinal healthcare record from the mapping and the content ingested from said plurality of connected nodes;

wherein said determining of a longitudinal healthcare record comprises determining provenance of at least one healthcare record; and wherein said determining of provenance comprises: probing or scanning nodes in said plurality of connected nodes for at least one archived healthcare record of a patient, determining connectivity of the probed or scanned nodes, and adding to the seed set a mapping of the connectivity of the probed or scanned nodes;

ascertaining if an archived healthcare record for said patient has propagated to a next node in the plurality of connected nodes based on said mapping of a plurality of connected nodes;

wherein to determine provenance comprises mapping backup or mirror nodes.

10. The method according to claim 9, further comprising:
identifying a source node in said plurality of connected nodes for a particular archived healthcare record.

11. The method according to claim 10, further comprising:
for said particular archived healthcare record, mapping at least one upstream record at an upstream node in said plurality of connected nodes supporting said particular archived healthcare record.

12. The method according to claim 11, wherein the particular archived healthcare record comprises one or more of: an exact copy of said upstream healthcare record, a transformed version of the upstream healthcare record, or a subset of data contained in said upstream healthcare record.

13. The method according to claim 11, further comprising:
accessing a graph comprising data flow connecting a plurality of related, archived healthcare records constructed from said mapping of a plurality of connected nodes.

14. The method according to claim 13, wherein said longitudinal healthcare record comprises a representation through time of data available from said plurality of related, archived healthcare records for a patient.

15. The method according to claim 9, further comprising:
mapping at least one modality to at least one of said plurality of connected nodes; and probing at least one node in said plurality of connected nodes for a specific data-type based on at least one modality of said at least one node.

16. A system comprising:
at least one processor; and
a memory device operatively connected to the at least one processor;

wherein, responsive to execution of program instructions accessible to the at least one processor, the at least one processor is configured to:

access a mapping of a plurality of connected nodes, said mapping being discovered via a network scan based on a seed set, said plurality of connected nodes storing a plurality of archived healthcare records, the seed set comprising an initial mapped set of nodes;

access content and ingested from said plurality of connected nodes; and determine a longitudinal healthcare record from the mapping and the content ingested from said plurality of connected nodes;

wherein to determine a longitudinal healthcare record comprises determining provenance of at least one healthcare record; and wherein to determine provenance comprises: probing or scanning nodes in said plurality of connected nodes for at least one archived healthcare record of a patient, determining connectivity of the probed or scanned nodes, and adding to the seed set a mapping of the connectivity of the probed or scanned nodes;

ascertaining if an archived healthcare record for said patient has propagated to a next node in the plurality of connected nodes based on said mapping of a plurality of connected nodes;

wherein to determine provenance comprises mapping backup or mirror nodes.

* * * * *